US006632660B2

(12) United States Patent
Ramstad

(10) Patent No.: US 6,632,660 B2
(45) Date of Patent: Oct. 14, 2003

(54) PETAL-ARRAY SUPPORT FOR USE WITH MICROPLATES

(75) Inventor: Paul O. Ramstad, San Jose, CA (US)

(73) Assignee: Applera Corporation, Foster City, CA (US)

(*) Notice: Subject to any disclaimer, the term of this patent is extended or adjusted under 35 U.S.C. 154(b) by 19 days.

(21) Appl. No.: 10/038,974

(22) Filed: Jan. 4, 2002

(65) Prior Publication Data

US 2003/0129741 A1 Jul. 10, 2003

(51) Int. Cl.[7] ................................................ C12M 1/22
(52) U.S. Cl. ................................ 435/305.2; 435/288.4; 435/309.1; 435/395; 435/287.3
(58) Field of Search .............................. 435/287.3, 395, 435/288.4, 305.2, 309.1

(56) References Cited

U.S. PATENT DOCUMENTS 5,213,766 A 5/1993 Flesher et al.
5,437,979 A 8/1995 Rampal et al.
5,962,250 A 10/1999 Gavin et al.
6,124,092 A 9/2000 O'Neill et al.
6,340,589 B1 * 1/2002 Turner et al. ............ 435/287.2

FOREIGN PATENT DOCUMENTS

WO WO 99/21958 A1 5/1999

* cited by examiner

*Primary Examiner*—David A. Redding
(74) *Attorney, Agent, or Firm*—Jeffery D. Frazier

(57) ABSTRACT

The present invention provides, among other things, supports upon which one or more species can be adsorbed, captured, or immobilized for biochemical procedures. In various embodiments, the supports include a plurality of deformable petal-like members that provide binding sites for biochemical species. The invention provides an apparatus and method for the ready insertion of the petal-like members into respective wells of a multi-well microplate (e.g., a standard-format 96- or 384-well plate).

13 Claims, 6 Drawing Sheets

Figure 1A
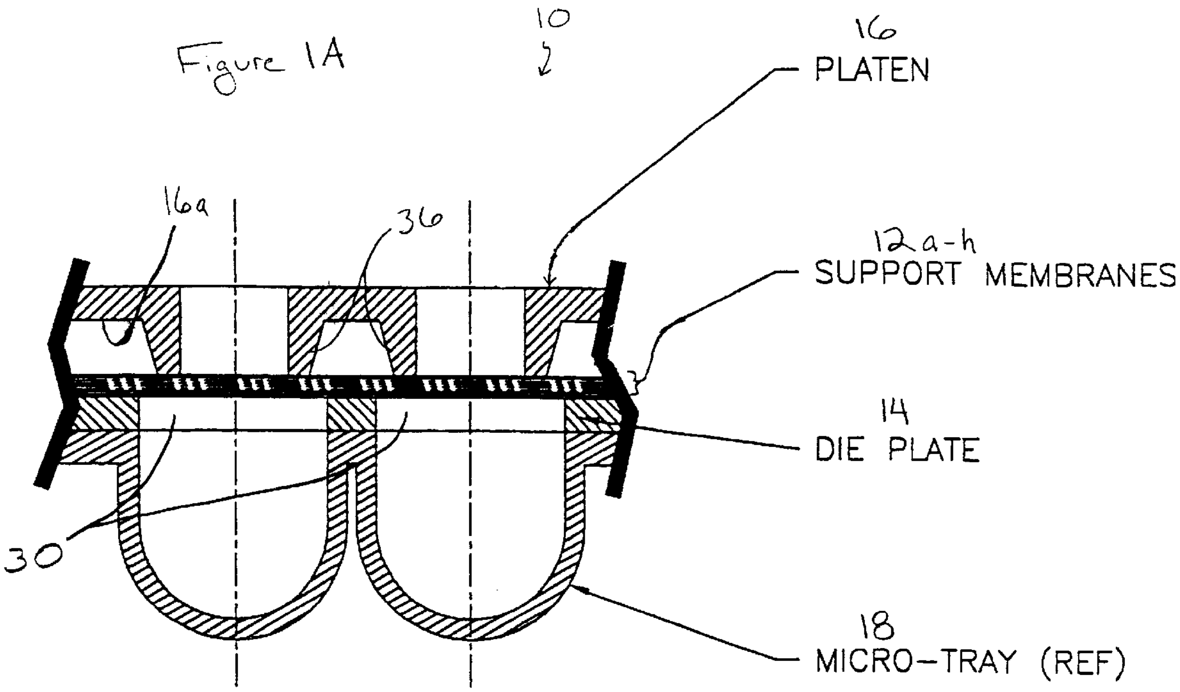
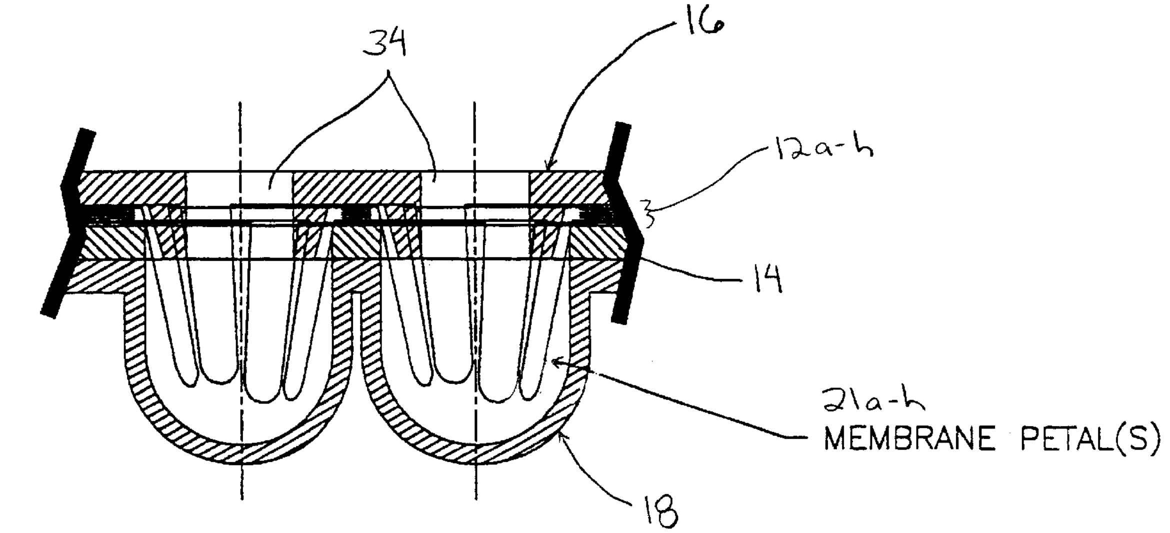
Figure 1B

Figure 4A
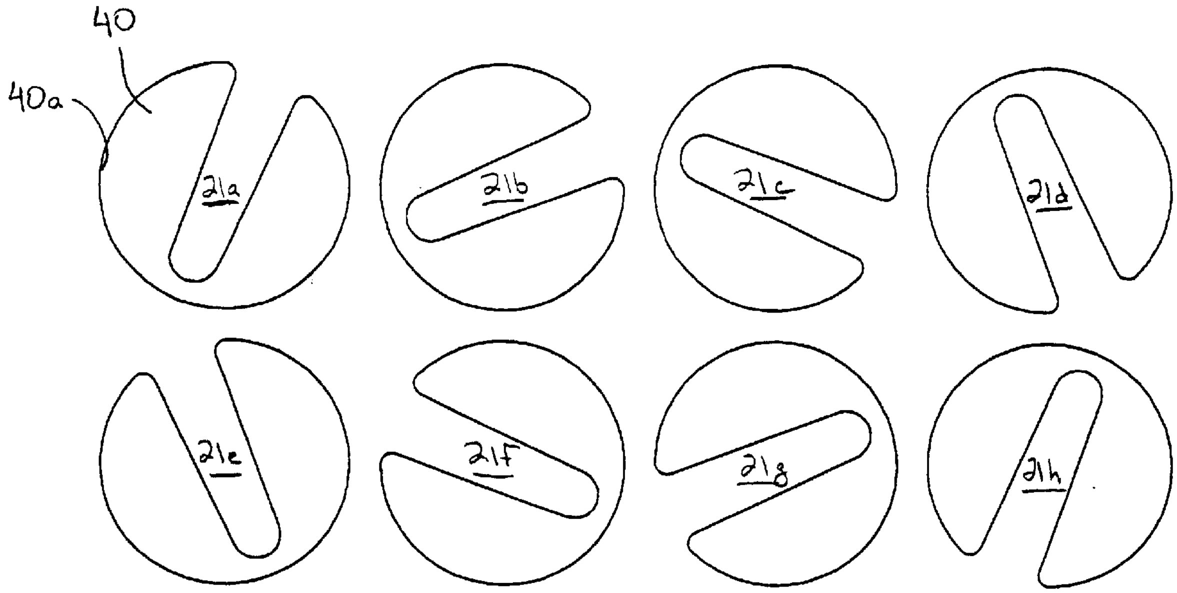
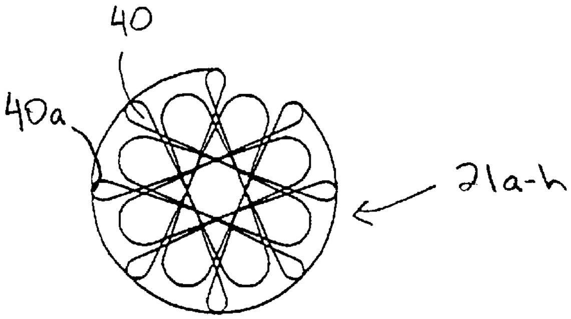
Figure 4B

Figure 5A
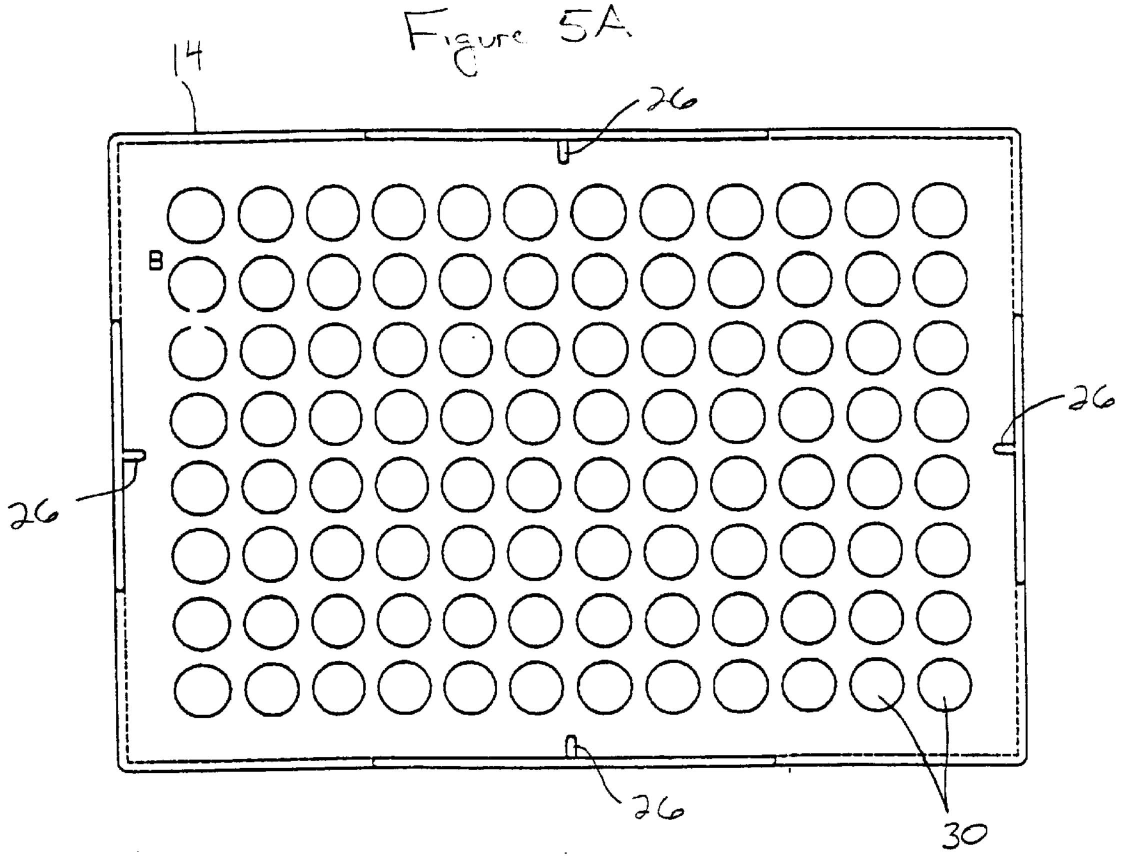
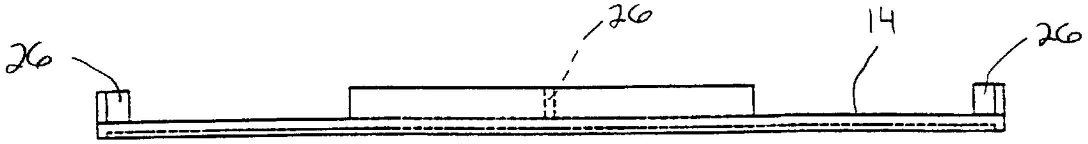
Figure 5B

Figure 6A
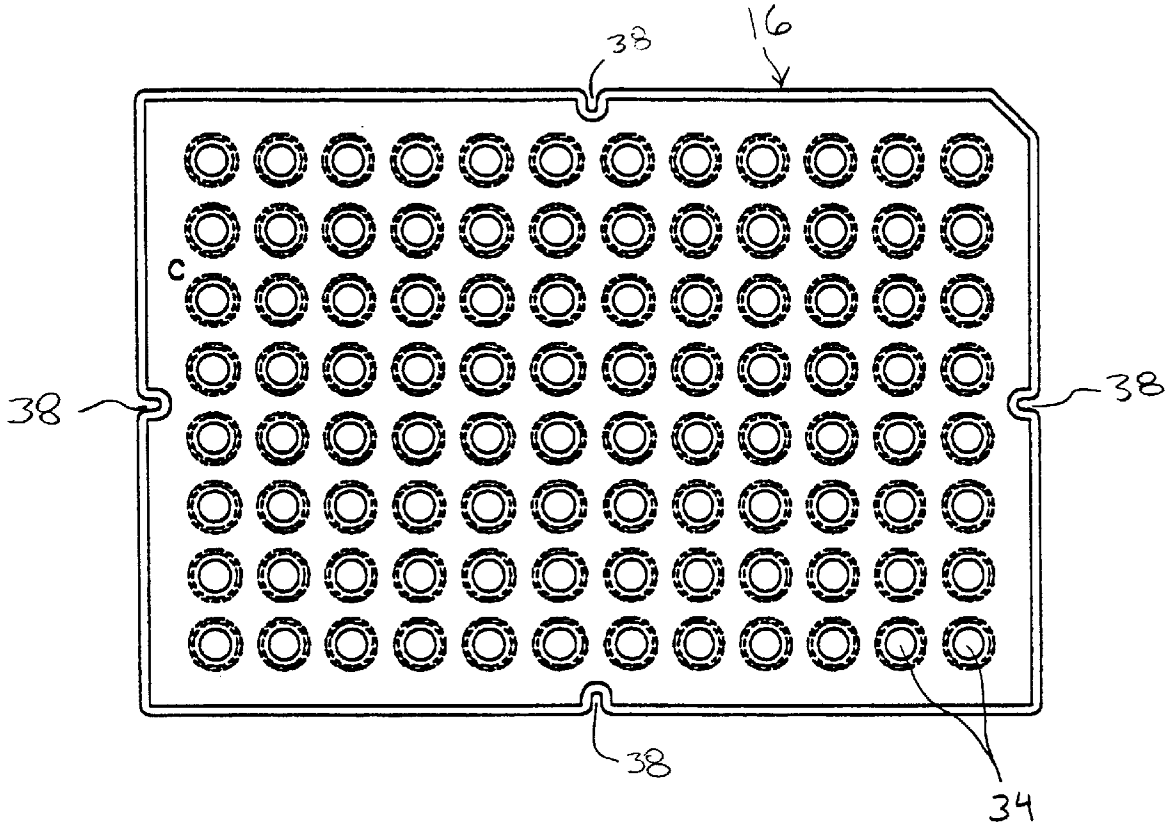
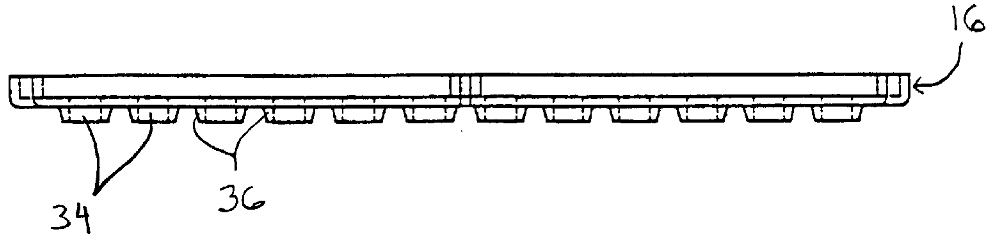
Figure 6B

PETAL-ARRAY SUPPORT FOR USE WITH MICROPLATES

FIELD OF THE INVENTION

The present invention relates to devices and methods for use in biochemical procedures, and to solid supports upon which one or more species can be immobilized.

BACKGROUND OF THE INVENTION

There has been a desire in recent years to develop methods for reversibly attaching biochemicals such as terminators or primers to a solid support. Various means have been considered for capturing and releasing nucleotides from a support, and ultimately delivering them to a specific site. Applications include hybridizing individual biological samples to mixed terminators that have been placed in the wells of microtiter plates, and then eluting the labeled nucleotide chains from their support for use in multiple sequencing reactions. Multiplex sequencing has the potential to significantly decrease sample handling and associated consumable costs for sample preparation for large-scale sequencing and genetic analysis projects. In order to selectively retrieve or "fish out" separate samples, the use of modified solid supports has been investigated.

SUMMARY OF THE INVENTION

Aspects of the present invention relate to, among other things, apparatus and methods providing an array of binding sites within the wells of a microplate (e.g., a standard-format, 96- 384-well plate). According to various embodiments, such binding sites comprise an array of petal-like members adapted for insertion into a corresponding array of reaction wells. Further aspects of the invention relate to, among other things, apparatus and methods facilitating the release of labeled monomers from a support, also within the microplate format.

Various embodiments provide an analyte-manipulation apparatus. The apparatus can include, for example, a plurality of wells defining an array, wherein each of the wells includes a rim defining an opening at an upper end thereof, with the openings being disposed within a first plane. The apparatus can further include a sheet-like support including a plurality of petal-like members integrally formed therein at positions corresponding to the wells of the array, with the support being disposed along a second plane above and substantially parallel to the first plane, and with at least one of the petal-like members being positioned near each one of the openings. In various embodiments, each of the petal-like members is movable between (i) a first position, substantially within the second plane, and (ii) a second position, at least partially disposed outside of the second plane and extending at least partially into a nearby well via a respective opening. The apparatus can further include a platen including a major surface facing the support, and a plurality of ring-like projections extending outwardly from the major surface, with the platen being adapted for movement toward and away from the support, whereby upon moving the platen toward the support, the projections can pressingly engage the petal-like members, thereby deflecting the petal-like members from the first position to the second position.

In various embodiments, the apparatus further includes a die plate disposed between the support and the rims, with the die plate including an array of apertures extending therethrough, and with each of the apertures being disposed at a position corresponding to a respective one of the wells of the array.

According to various embodiments, the platen and each of the ring-like projections defines a passage extending longitudinally through each ring-like projection and through the platen. Such passage can be quite useful. For example, with the petal-like members being deflected into their respective wells, an instrument such as a pipette or the like can be inserted through the passage to access the interior region of any one or more of the wells. For example, sample and/or reagent can be deposited into one or more selected wells, e.g., using such an instrument, via such passage. In addition, or in the alternative, sample and/or reagent can be withdrawn from one or more selected wells, e.g., using such an instrument, via such passage.

In various embodiments, at least a portion of the petal-like members can be chemically treated.

According to various embodiments, one or more of the petal-like members can include one or more biochemicals immobilized thereon. Such biochemicals can include, for example, one or more nucleic acids. In various embodiments, such biochemicals comprise one or more DNA-sequencing reagents, such as terminators, primers, or a combination thereof.

According to various embodiments, each support is a single-layer film or membrane material.

In various embodiments, the petal-like members are resiliently deformable, tending to return to the first position after having been deflected therefrom.

According to various embodiments, each support includes one or more registration features (e.g., one or more slots formed in each of the sheets) facilitating alignment of the supports with respect to the microplate.

In various embodiments, each of the ring-like projection tapers in a direction away from the major surface.

Various embodiments provide an analyte-manipulation apparatus including a plurality of wells defining an array, with each of the wells including an opening at an upper end thereof. The apparatus can further include a stack of sheet-like supports disposed above the openings, with each support of the stack including a plurality of petal-like members integrally formed therein, and with each petal-like member of each support being disposed at a position corresponding to a respective one of the wells of the array. In various embodiments, each of the petal-like members is movable between (i) a first position, outside of a corresponding respective well, and (ii) a second position, extending at least partially into such corresponding respective well. The apparatus can further include a platen including a major surface facing the support, and a plurality of ring-like projections extending outwardly from the major surface, with the platen being adapted for movement toward and away from the support, whereby upon moving the platen toward the support, the projections can pressingly engage the petal-like members, thereby deflecting the petal-like members from the first position to the second position.

According to various embodiments, the stack includes at least three (e.g., 3, 4, 5, 6, 7, 8, 9, 10, or more) of the supports.

In various embodiments, one or more of the petal-like members includes one or more biochemicals (e.g., nucleic acids) immobilized thereon.

According to various embodiments, each support is a single-layer film or membrane material.

According to various embodiments, the platen and each of the ring-like projections defines a passage extending longitudinally through each ring-like projection and through the platen. Such passage can be quite useful. For example, with the petal-like members being deflected to the second position, an instrument such as a pipette or the like can be inserted through the passage to access the interior region of any one or more of the wells. For example, sample and/or reagent can be deposited into one or more selected wells, e.g., using such an instrument, via such passage. In addition, or in the alternative, sample and/or reagent can be withdrawn from one or more selected wells, e.g., using such an instrument, via such passage.

Various embodiments provide a method for biochemical interactions.

In certain embodiments, such a method includes:

immobilizing one or more selected biochemicals on a plurality of petal-like members, wherein the petal-like members are disposed in an array on a support;

introducing one or more reagents into a plurality of wells, wherein the wells are disposed in an array corresponding to the array of petal-like members;

positioning the petal-like members above the plurality of wells, so that each petal-like member is situated above a corresponding one of the plurality of wells;

pressingly engaging the petal-like members from a side opposite that of the wells, so that the petal-like members are simultaneously moved into their corresponding wells, thereby contacting the one or more reagents; and permitting a biochemical interaction to take place involving the one or more selected biochemicals and the one or more reagents.

According to various embodiments, the one or more selected biochemicals comprise nucleic acids.

In various embodiments, the one or more selected biochemicals comprise one or more DNA-sequencing reagents, such as terminators, primers, or a combination thereof.

Other various embodiments of such a method include:

providing a plurality of petal-like members, wherein the petal-like members are disposed in an array on a support;

providing a microplate including a plurality of wells disposed in an array corresponding to the array of petal-like members;

placing one or more selected biochemicals in the wells of the microplate;

positioning the petal-like members above the microplate, so that each petal-like member is situated above a corresponding one of the plurality of wells;

pressingly engaging the petal-like members from a side opposite that of the wells, so that the petal-like members are simultaneously moved into their corresponding wells, thereby contacting the one or more selected biochemicals therein;

immobilizing the one or more selected biochemicals in the wells upon the petal-like members; and withdrawing the petal-like members from the wells, with the one or more selected biochemicals remaining immobilized thereon.

In various embodiments, such method further comprises:

providing a second microplate including a plurality of wells disposed in an array corresponding to the array of petal-like members;

providing one or more selected reagents in the wells of the second microplate;

positioning the petal-like members above the second microplate, so that each petal-like member is situated above a corresponding one of the plurality of wells;

pressingly engaging the petal-like members from a side opposite that of the second microplate, so that the petal-like members are simultaneously moved into their corresponding wells, thereby contacting the one or more reagents therein; and permitting a biochemical interaction to take place involving the one or more selected biochemicals and the one or more selected reagents.

In other various embodiments, such method further comprises:

providing a second microplate including a plurality of wells disposed in an array corresponding to the array of petal-like members;

positioning the petal-like members above the second microplate, so that each petal-like member is situated above a corresponding one of the plurality of wells;

pressingly engaging the petal-like members from a side opposite that of the second microplate, so that the petal-like members are simultaneously moved into their corresponding wells, thereby contacting the one or more reagents therein; and releasing the one or more selected biochemicals from the petal-like members into the wells.

BRIEF DESCRIPTION OF THE DRAWINGS

The structure and manner of operation of the invention may further be understood by reference to the following description taken in conjunction with the accompanying drawings, in which identical reference numerals identify identical or similar elements, and in which:

FIGS. 1A and 1B are partial side-sectional views of an apparatus according to various embodiments.

FIGS. 4A and 4B are enlarged top plan views showing a plurality of petal-like members, each taken from a respective support of an aligned stack of eight supports, individually and superposed, respectively.

FIGS. 5A and 5B show a die plate, according to various embodiments, in top plan and side elevational views, respectively.

FIGS. 6A and 6B show a platen, according to various embodiments, in top plan and side elevational views, respectively.

DETAILED DESCRIPTION

Reference will now be made to various embodiments of the invention, examples of which are illustrated in the accompanying drawings. While the invention will be described in conjunction with various embodiments, it will be understood that they are not intended to limit the invention. On the contrary, the invention is intended to cover alternatives, modifications, and equivalents, which may be included within the invention as defined by the appended claims.

Provided herein, among other things, are means to provide an array of solid supports or binding sites within the wells of a microplate (e.g., a standard-format, 96- or 384-well plate), and means to facilitate the release of species such as labeled monomers from their support (which can also be within the microplate format).

Figure 2:
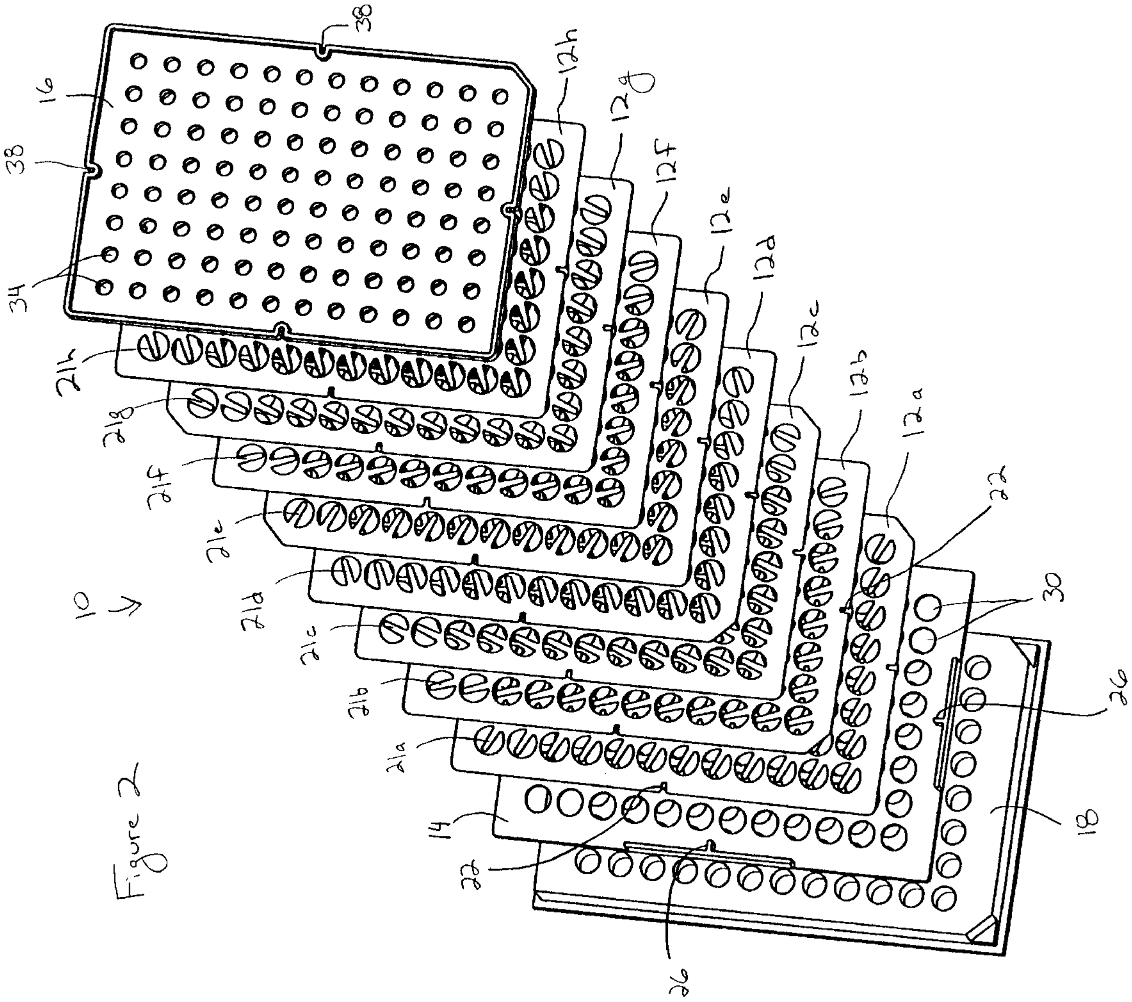
FIG. 2 is an exploded, perspective view of the apparatus shown in FIG. 1A.

According to various embodiments, and with initial reference to FIGS. 1A and 2, an apparatus of the invention, denoted generally at 10, includes one or more supports, such as the stack of sheet-like supports indicated at 12*a–h*. In the illustrated arrangement, the supports 12*a–h* are situated between a die plate 14 and a platen 16.

The supports 12*a–h* can be formed of any suitable material, such as a membrane or film material, or the like. In various embodiments, each of the supports 12*a–h* comprises a polymeric film, such as a polycarbonate or polystyrene film having a thickness of between about 0.001" to about 0.010" (e.g., about 0.004"). The film can be textured to increase its effective surface area. In various embodiments, each sheet-like support is a die-cut, chemically-treated, membrane or film support.

Figure 3:
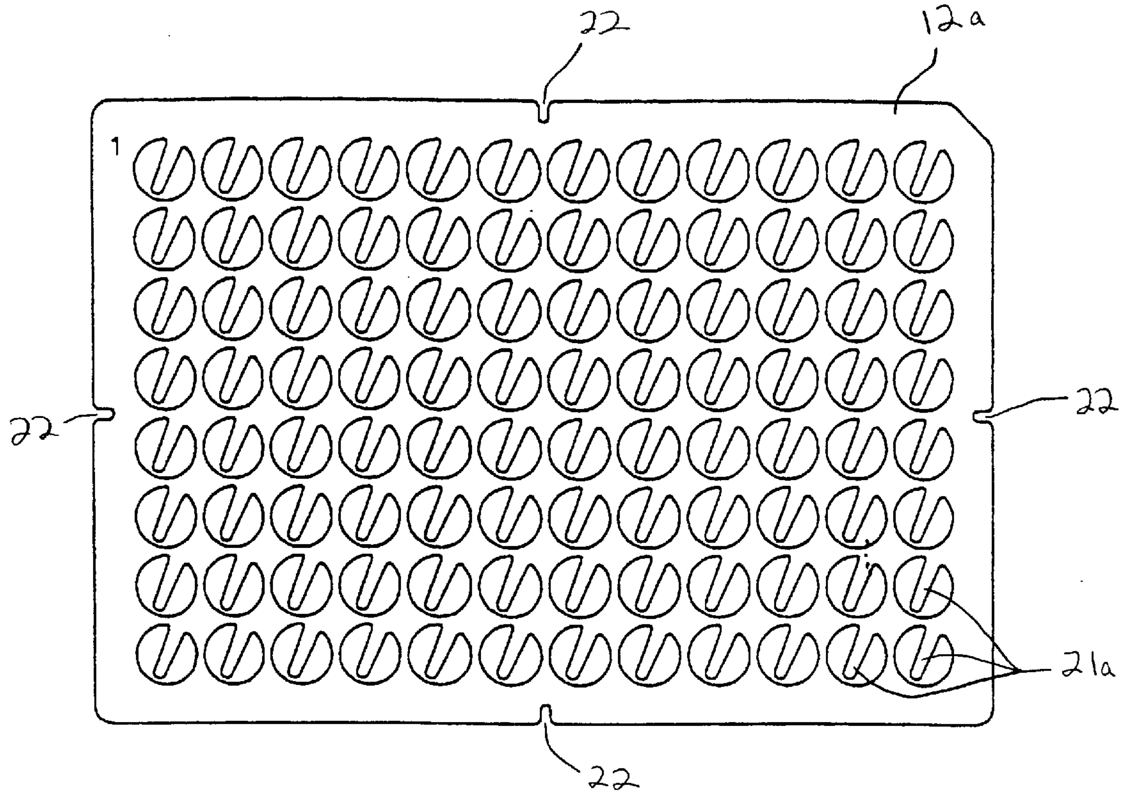
FIG. 3 is a top plan view showing a support including petal-like members, according to various embodiments.

FIG. 3 shows a single sheet-like support, 12*a*, from the stack of supports 12*a–h* of FIG. 2, in top plan view. Support 12*a* is configured with outer dimensions generally like that of the top surface of a microplate with which it is to be used. Support 12*a* is die-cut to provide an array of petal-like members, denoted as 21*a*. The petal-like members are arranged in an array corresponding to an array of wells with which the support is to be used (e.g., a regular 25 rectangular array). In the illustrated arrangement, the petal-like members are arranged in a 12×8 array, with adjacently disposed petal-like members being spaced 0.9 cm center-to-center. Other array configurations are contemplated herein (e.g., a 24×16 array, with adjacently disposed petal-like members being spaced 0.45 cm center-to-center).

Each of the sheet-like supports 12*a–h* can include one or more location features to facilitate alignment with respect to the other system components. For example, as shown in FIGS. 2 and 3, slots 22 can be formed at selected locations along the edge regions of each of the supports 12*a–h*. The slots 22 can be positioned and configured to mate with complementary-shaped regions of one or more of the microplate 18, die plate 14, and/or platen 16. For example, FIG. 2 shows a protrusion 26 for such purpose formed at a mid-point along each edge region of the die plate 14.

It is to be noted that, according to various embodiments, the directionality of all the petal-like members of any one of the supports is the same. That is, for any given support, the petal-like members "point" in the same direction. It is further to be noted that, in such embodiments, the directionality of the petal-like members differs between any two of the supports. That is, the petal-like members of any one support point in a direction that differs from that of any of the other supports. In the embodiment of FIG. 2, for example, it can be seen that each support includes a petal-like member disposed at a position that is radially distinct from the petal-like members of the other supports of the stack. FIGS. 4A and 4B show petal-like members 21*a*–21*h* from a selected coordinate (e.g., row 1, column 1) of each of the eight supports 12*a–h* of the stack from FIG. 2, respectively. In other words, each of the eight depicted petal-like members can be considered as being that found at row 1, column 1 from a respective one of the eight supports 12*a–h* of the stack. The petal-like members are shown, in FIGS. 4A and 4B, with each in the orientation it would have when the eight supports are stacked and aligned for use, such as shown in FIGS. 1A and 2. As can be seen, each of the die-cut portions defines a circular open region 40 having a circumferential edge 40*a*, with its respective petal-like member extending into the circular open region from a unique position along the circumferential edge. FIG. 4B shows the petal-like members from FIG. 4A superposed one over the other, as they would be when disposed in an aligned stack. The eight petal-like members in FIG. 4B can be seen extending inwardly into a common circular open region from regularly spaced positions about the circumferential edge of the circular open region.

According to various embodiments, each of the petal-like members 21*a–h* is deformable from a normal position, substantially within a plane defined by the sheet, to a second position, at least partially disposed outside of such plane. In some embodiments, the petal-like members are resilient, such that they return to their normal position after a deforming force in discontinued. Due to their deformable quality, it will be appreciated that, by applying a downwardly directed force against the petal-like members, they can be deflected from their normal position to such second position (e.g., below the plane of the support). Upon removing the force, resilient petal-like members will be able to return substantially to their normal position.

FIGS. 5A–B and 6A–B show, respectively, the die plate 14 and platen 16 in top plan and side elevational views.

As indicated above, the die plate 14 can include protrusions 26 for properly locating and aligning one or more supports thereon by way slots, such as slots 22 in supports 12*a–h*. It will be appreciated that such location features further facilitate location of the array of petal-like members elements directly over their respective well openings in a microplate. The die plate 14 additionally includes an array of holes or apertures 30 that are concentric, and directly correspond to, the wells of the microplate 18. The die plate can also include features that align it relative to the microplate, and/or to the platen.

With reference to FIG. 6, the platen 16 includes passages or through-holes 34 that are concentric, and directly correspond to, the wells of the microplate 18. Except for such through-holes, the platen is configured to substantially cover the supports. The platen 16 further includes ring-like projections 36 (FIG. 6B) extending from a major surface thereof, denoted as 16*a*, with each ring-like projection circumscribing, and further defining, a respective one of the through-holes 34. Such construction permits access to the individual wells of the microplate from a region extending above each of the wells.

As can be seen in FIGS. 1A and 1B, the outer circumferential region of each ring-like projection 36 is configured with a taper along a direction extending away from the major surface 16*a* of the platen 16. The taper facilitates placement and seating of each ring-like projection in a corresponding aperture 30 of the die plate 14 upon bringing the platen 16 and die plate 14 together (see FIG. 1B), as described further below. The platen 16 further includes slots, as at in FIG. 6B, having a shape similar to the slots 22 of the supports 12*a–h*, which assist in properly locating and aligning the platen 16 over the die plate 14 by mating with the projections 26 of the die plate 14.

The die plate 14, platen 16, and microplate 18 can be formed by any conventional means, with injection molding being one suitable technique. According to various embodiments, these components can be constructed of any substantially rigid, water-insoluble, fluid-impervious material that is substantially chemically non-reactive with the biochemicals, samples, reagents, etc. intended for use therewith. The term "substantially rigid" as used herein is intended to mean that the material will resist deformation or warping under a light mechanical or thermal load, although the material may be somewhat elastic. Suitable materials include acrylics, polycarbonates, polypropylenes and polysulfones.

With regard to the microplate 18, various embodiments of the invention contemplate the use of injection molded rectangular plastic plates, the length and width of which conform to the commonly used standard of 5.03"×3.37" (127.8 mm and 85.5 mm). In the illustrated embodiments, the wells are formed integrally with such a plate, arranged in a 12×8 regular rectangular array spaced 0.9 cm center-to-center. Although the illustrated embodiments show arrangements configured in accordance with the popular 96-well format, the invention also contemplates any other reasonable number of wells (e.g., 12, 24,48, 384, etc.) laid out in any suitable configuration.

In operation, a die plate can be positioned over a multi-well microplate, with each aperture of the die plate located over a corresponding one of the wells of the microplate. A plurality of sheet-like supports can be stacked upon the die plate. Alignment of the supports with respect to the die plate can be facilitated by way of slots formed in the supports and mating projections extending from atop the die plate. Each support of the stack can include a plurality of petal-like members, with each petal-like member of each support being disposed at a position corresponding to a respective one of the wells of the microplate. Each of the petal-like members can be moved between (i) a first position, outside of a corresponding well, and (ii) a second position, extending at least partially into such corresponding well. A platen can be placed over the stack of supports. The platen can include a major surface facing the support, and a plurality of ring-like projections extending outwardly from the major surface. The platen can be moved toward and away from the support. Upon moving the platen toward the support, the projections can pressingly engage the petal-like members, thereby deflecting the petal-like members from the first to the second position, such as is depicted in FIG. 1B. More particularly, in various embodiments, the ring-like projections of the platen can pressingly engage and deflect the petal-like members of the sheets against the holes in the die plate, and into the wells of the microplate, whereat they can chemically interact with the contents of the individual wells.

In various embodiments, one or more nucleic acids can be immobilized on the petal-like members. The petal-like members can then be introduced into respective reaction wells that can contain reagents for carrying out polymerase chain reaction (PCR). PCR can then be carried out. Analysis of the PCR product(s) can then be performed.

According to various embodiments, the binding site array assembly can be constructed to utilize a plurality of support membrane sheets between the die and platen to maximize sample exposure, when it is used to "fish" out matching sequences from the contents of the microplate wells. Each "exposed" membrane sheet can then be removed from the assembly, and reassembled between a second die and platen for elution of the labeled samples into another (clean) microplate.

According to various alternative embodiments, the upper portions of the microplate wells can be configured to act in place of the die plate, thus eliminating the die plate from the above-described assembly. Many varieties of microplates, available from different suppliers, can be accommodated by the incorporation of a spring-loaded centering means within the basic assembly.

It will be appreciated by those skilled in the art that the present invention provides, among other things, a means for delivering terminators, or primers, for use in DNA sequencing; a facility for the exposure of multiple discreet supports to an array of individual samples; and, a tool for moving and/or transferring large numbers of labeled samples at a time. The present invention further provides, among other things, the ability to capture nucleotides, or other biological samples, to multiple binding sites within a standard laboratory microplate format, and their subsequent release from the support, also within the microplate format.

The present invention provides for integrating a plurality of discreet labeled petal-like members (e.g., 96) and their support into a single deformable sheet-like film or membrane. This design eliminates many handling and alignment issues associated with stacking, and placing as many as twelve post/array assemblies, with densely packed probes, into the 96 distinct wells of a standard microtiter plate.

All publications and patent applications referred to herein are hereby incorporated by reference to the same extent as if each individual publication or patent application was specifically and individually indicated to be incorporated by reference.

Those having ordinary skill in the art will clearly understand that many modifications are possible in the above preferred embodiments without departing from the teachings thereof. All such modifications are intended to be encompassed within the following claims.

It is claimed:

1. An analyte-manipulation apparatus, comprising:

a plurality of wells defining an array, wherein each of said wells includes a rim defining an opening at an upper end thereof, with said openings being disposed within a first plane;

a support including a plurality of petal-shaped members integrally formed therein at positions corresponding to said wells of said array, with said support being disposed along a second plane above and substantially parallel to said first plane, and with at least one of said petal-shaped members being positioned near each one of said openings;

wherein each of said petal-shaped members is movable between (i) a first position, substantially within said second plane, and (ii) a second position, at least partially disposed outside of said second plane and extending at least partially into a nearby well via a respective opening;

a platen including a major surface facing said support, and a plurality of ring-shaped projections extending outwardly from said major surface, with said platen being adapted for movement toward and away from said support, whereby upon moving said platen toward said support, said projections can pressingly engage said petal-shaped members, thereby deflecting said petal-shaped members from said first position to said second position; and a die plate disposed between said support and said rims, said die plate including an array of apertures extending therethrough, each of said apertures being disposed at a position corresponding to a respective one of said wells of said array.

2. An analyte-manipulation apparatus, comprising:

a plurality of wells defining an array, wherein each of said wells includes a rim defining an opening at an upper end thereof, with said openings being disposed within a first plane;

a support including a plurality of petal-shaped members integrally formed therein at positions corresponding to said wells of said array, with said support being disposed along a second plane above and substantially parallel to said first plane, and with at least one of said petal-shaped members being positioned near each one of said openings;

wherein each of said petal-shaped members is movable between (i) a first position, substantially within said second plane, and (ii) a second position, at least partially disposed outside of said second plane and extending at least partially into a nearby well via a respective opening; and a platen including a major surface facing said support, and a plurality of ring-shaped projections extending outwardly from said major surface, with said platen being adapted for movement toward and away from said support, whereby upon moving said platen toward said support, said projections can pressingly engage said petal-shaped members, thereby deflecting said petal-shaped members from said first position to said second position;

wherein at least a portion of said petal-shaped members are chemically treated.

3. An analyte-manipulation apparatus, comprising:

a plurality of wells defining an array, wherein each of said wells includes a rim defining an opening at an upper end thereof, with said openings being disposed within a first plane;

a support including a plurality of petal-shaped members integrally formed therein at positions corresponding to said wells of said array, with said support being disposed along a second plane above and substantially parallel to said first plane, and with at least one of said petal-shaped members being positioned near each one of said openings;

wherein each of said petal-shaped members is movable between (i) a first position, substantially within said second plane, and (ii) a second position, at least partially disposed outside of said second plane and extending at least partially into a nearby well via a respective opening; and a platen including a major surface facing said support, and a plurality of ring-shaped projections extending outwardly from said major surface, with said platen being adapted for movement toward and away from said support, whereby upon moving said platen toward said support, said projections can pressingly engage said petal-shaped members, thereby deflecting said petal-shaped members from said first position to said second position; and wherein one or more of said petal-shaped members includes one or more biochemicals immobilized thereon.

4. The apparatus of claim 3, wherein said one or more biochemicals comprise nucleic acids.

5. The apparatus of claim 3, wherein said one or more biochemicals comprise one or more DNA-sequencing reagents.

6. The apparatus of claim 5, wherein said one or more DNA-sequencing reagents are selected from the group consisting of terminators, primers, and a combination thereof.

7. An analyte-manipulation apparatus, comprising:

a plurality of wells defining an array; each of said wells including an opening at an upper end thereof;

a stack of at least three supports disposed above said openings, each support of said stack including a plurality of petal-shaped members integrally formed therein, and each petal-shaped member of each support being disposed at a position corresponding to a respective one of said wells of said array;

wherein each of said petal-shaped members is movable between (i) a first position, outside of a corresponding respective well, and (ii) a second position, extending at least partially into such corresponding respective well; and a platen including a major surface facing said support, and a plurality of ring-shaped projections extending outwardly from said major surface, with said platen being adapted for movement toward and away from said support, whereby upon moving said platen toward said support, said projections can pressingly engage said petal-shaped members, thereby deflecting said petal-shaped members from said first position to said second position;

wherein said petal-shaped members include one or more biochemicals immobilized thereon.

8. A method for biochemical interactions, comprising:

immobilizing one or more selected biochemicals on a plurality of petal-shaped members, wherein the petal-shaped members are disposed in an array on a support;

introducing one or more reagents into a plurality of wells, wherein the wells are disposed in an array corresponding to the array of petal-shaped members;

positioning the petal-shaped members above the plurality of wells, so that each petal-shaped member is situated above a corresponding one of the plurality of wells;

pressingly engaging the petal-shaped members from a side opposite that of the wells, so that the petal-shaped members are simultaneously moved into their corresponding wells, thereby contacting the one or more reagents; and permitting a biochemical interaction to take place involving the one or more selected biochemicals and the one or more reagents.

9. The method of claim 8, wherein said one or more selected biochemicals comprise nucleic acids.

10. The method of claim 8, wherein said one or more selected biochemicals comprise one or more DNA-sequencing reagents.

11. The method of claim 10, wherein said one or more DNA-sequencing reagents are selected from the group consisting of terminators, primers, and a combination thereof.

12. A method for biochemical interactions, comprising:

providing a plurality of petal-shaped members, wherein the petal-shaped members are disposed in an array on a support;

providing a microplate including a plurality of wells disposed in an array corresponding to the array of petal-shaped members;

placing one or more selected biochemicals in the wells of the microplate;

positioning the petal-shaped members above the microplate, so that each petal-shaped member is situated above a corresponding one of the plurality of wells;

pressingly engaging the petal-shaped members from a side opposite that of the wells, so that the petal-shaped members are simultaneously moved into their corresponding wells, thereby contacting the one or more selected biochemicals therein;

immobilizing said one or more selected biochemicals in the wells upon the petal-shaped members;

withdrawing the petal-shaped members from the wells, with the one or more selected biochemicals remaining immobilized thereon;

providing a second microplate including a plurality of wells disposed in an array corresponding to the array of petal-shaped members;

providing one or more selected reagents in the wells of the second microplate;

positioning the petal-shaped members above the second microplate, so that each petal-shaped member is situated above a corresponding one of the plurality of wells;

pressingly engaging the petal-shaped members from a side opposite that of the second microplate, so that the petal-shaped members are simultaneously moved into their corresponding wells, thereby contacting the one or more reagents therein; and permitting a biochemical interaction to take place involving the one or more selected biochemicals and the one or more selected reagents.

13. A method for biochemical interactions, comprising:

providing a plurality of petal-shaped members, wherein the petal-shaped members are disposed in an array on a support;

providing a microplate including a plurality of wells disposed in an array corresponding to the array of petal-shaped members;

placing one or more selected biochemicals in the wells of the microplate;

positioning the petal-shaped members above the microplate, so that each petal-shaped member is situated above a corresponding one of the plurality of wells;

pressingly engaging the petal-shaped members from a side opposite that of the wells, so that the petal-shaped members are simultaneously moved into their corresponding wells, thereby contacting the one or more selected biochemicals therein;

immobilizing said one or more selected biochemicals in the wells upon the petal-shaped members;

withdrawing the petal-shaped members from the wells, with the one or more selected biochemicals remaining immobilized thereon;

providing a second microplate including a plurality of wells disposed in an array corresponding to the array of petal-shaped members;

positioning the petal-shaped members above the second microplate, so that each petal-shaped member is situated above a corresponding one of the plurality of wells;

pressingly engaging the petal-shaped members from a side opposite that of the second microplate, so that the petal-shaped members are simultaneously moved into their corresponding wells, thereby contacting the one or more reagents therein; and releasing the one or more selected biochemicals from the petal-shaped members into the wells.

* * * * *